US012754548B2

(12) United States Patent
Su et al.

(10) Patent No.: US 12,754,548 B2
(45) Date of Patent: Oct. 6, 2026

(54) PATH PLANNING METHOD AND AUTONOMOUS TRAVELING ROBOT

(71) Applicant: Wistron Corporation, New Taipei City (TW)

(72) Inventors: Ting Chieh Su, New Taipei City (TW); Hsien Chun Cheng, New Taipei City (TW); Chen Wei Yang, New Taipei City (TW); Tsun-Hsien Kuo, New Taipei City (TW)

(73) Assignee: Wistron Corporation, New Taipei City (TW)

( * ) Notice: Subject to any disclaimer, the term of this patent is extended or adjusted under 35 U.S.C. 154(b) by 355 days.

(21) Appl. No.: 18/185,404

(22) Filed: Mar. 17, 2023

(65) Prior Publication Data

US 2024/0241517 A1 Jul. 18, 2024

(30) Foreign Application Priority Data

Jan. 17, 2023 (TW) ................................ 112101965

(51) Int. Cl.
*G05D 1/00* (2024.01)
*A61L 2/10* (2026.01)

(52) U.S. Cl.
CPC .............. *G05D 1/0214* (2013.01); *A61L 2/10* (2013.01); *G05D 1/0231* (2013.01); *G05D 1/0274* (2013.01); *A61L 2202/16* (2013.01)

(58) Field of Classification Search
CPC .. G05D 1/0214; G05D 1/0231; G05D 1/0274; A61L 2/10; A61L 2202/16
USPC .......................................................... 701/23
See application file for complete search history.

(56) References Cited

U.S. PATENT DOCUMENTS

| | | | | |
|---|---|---|---|---|
| 4,674,048 | A * | 6/1987 | Okumura | B25J 9/1676 701/25 |
| 11,753,045 | B2 * | 9/2023 | Li | B60W 30/09 701/26 |
| 12,025,987 | B2 * | 7/2024 | Kolling | G05D 1/648 |

(Continued)

FOREIGN PATENT DOCUMENTS

| | | | | |
|---|---|---|---|---|
| CN | 109876968 A * | 6/2019 | | |
| CN | 111307156 A * | 6/2020 | | G01C 21/206 |

(Continued)

OTHER PUBLICATIONS

J. . -X. Xu and K. C. Kin, "Intelligent mobile robot path planning with fuzzy system approaches," Proceedings of IEEE 2nd International Workshop on Emerging Technologies and Factory Automation (ETFA '93), Palm Cove-Cairns, QLD, Australia, 1993, pp. 28-41, doi: 10.1109/ETFA.1993.396432. (Year: 1993).*

(Continued)

*Primary Examiner* — Abby J Flynn
*Assistant Examiner* — Merritt Levy
(74) *Attorney, Agent, or Firm* — JCIPRNET

(57) ABSTRACT

A path planning method and an autonomous traveling robot are provided. In the path planning method, a target area is obtained. A traveling path is decided by a safety distance. The traveling path is at least at the safety distance from an edge of the target area. The autonomous traveling robot is controlled to move by the traveling path. Accordingly, the operation efficiency can be improved.

14 Claims, 14 Drawing Sheets

(56) References Cited

U.S. PATENT DOCUMENTS

| | | | | |
|---|---|---|---|---|
| 2005/0075785 | A1* | 4/2005 | Gray | G05D 1/0274 701/410 |
| 2007/0061043 | A1* | 3/2007 | Ermakov | G05D 1/0274 700/263 |
| 2010/0141483 | A1* | 6/2010 | Thacher | G01S 13/931 340/989 |
| 2012/0101725 | A1* | 4/2012 | Kondekar | G05D 1/0219 701/445 |
| 2018/0281191 | A1* | 10/2018 | Sinyavskiy | A47L 11/4061 |
| 2022/0229438 | A1* | 7/2022 | Nabeta | G05D 1/0214 |
| 2024/0016074 | A1* | 1/2024 | Nishii | G05D 1/617 |

FOREIGN PATENT DOCUMENTS

| | | | | | |
|---|---|---|---|---|---|
| CN | 111562785 | A | * | 8/2020 | G05D 1/0287 |
| CN | 112703834 | | | 4/2021 | |
| CN | 114185351 | A | * | 3/2022 | |
| CN | 111694357 | B | * | 5/2022 | G05D 1/0217 |

OTHER PUBLICATIONS

Dong, Yong-feng, Xia, Hong-mei, Zhou, Yan-cong, Disordered and Multiple Destinations Path Planning Methods for Mobile Robot in Dynamic Environment, Journal of Electrical and Computer Engineering, 2016, 3620895, 10 pages, 2016. https://doi.org/10.1155/2016/3620895 (Year: 2016).*

Liu Y, et al. "A scheduling route planning algorithm . . . with an colony binary iterative optimization for unmanned aerial vehicle spraying in multiple tea fields". Front Plant Sci. Sep. 16, 2022; 13:998962. doi: 10.3389/fpls.2022.998962. PMID: 36186015; PMCID: PMC9523449. (Year: 2022).*

M. Bun, et al, "CFP RRT for an automatic robot in the narrow space . . . ," 2021 18th International Conference on Electrical Engineering/Electronics, Computer, Telecommunications and Information Technology (ECTI-CON), Chiang Mai, Thailand, 2021, pp. 737-741, doi: 10.1109/ECTI-CON51831.2021.9454754. (Year: 2021).*

R. Yang, P. Cai and L. Wang, "Comparison of Strategies for Optimizing Bi-RRT* on Mobile Robots," 2021 IEEE International Conference on Computer Science, Artificial Intelligence and Electronic Engineering (CSAIEE), SC, USA, 2021, pp. 328-334, doi: 10.1109/CSAIEE54046.2021.9543111. (Year: 2021).*

* cited by examiner

PATH PLANNING METHOD AND AUTONOMOUS TRAVELING ROBOT

CROSS-REFERENCE TO RELATED APPLICATION

This application claims the priority benefit of Taiwan application serial no. 112101965, filed on Jan. 17, 2023. The entirety of the above-mentioned patent application is hereby incorporated by reference herein and made a part of this specification.

BACKGROUND

Technical Field

The disclosure relates to an automatic control technology, and in particular to a path planning method and an autonomous traveling robot.

Description of Related Art

Currently, the autonomous traveling vehicle system may use simultaneous localization and mapping (SLAM) or a rail system to achieve autonomous traveling. At present, there are various applications using the autonomous traveling vehicle system, such as the ultraviolet-C (UVC) sterilizing robot. Different applications may face different difficulties. For example, due to the limitation of the mechanism design of the UVC sterilizing robot, the ultraviolet lamp tube can only irradiate toward a fixed direction, so when the robot is operating, the side irradiated by the ultraviolet lamp must face the sterilizing target. When the UVC sterilizing robot is operating, if the distance from the sterilizing target is too far, the sterilizing efficiency deteriorates. However, if the distance from the sterilizing target is too short, the robot may easily collide with the sterilizing target.

SUMMARY

The disclosure provides a path planning method and an autonomous traveling robot, which can plan a suitable route to improve the operating efficiency of the robot.

A path planning method of an embodiment of the disclosure includes (but not limited to) the following steps. A target area is obtained. A traveling path is decided by a safety distance. The traveling path is at least at the safety distance from an edge of the target area. An autonomous traveling robot being moved by the traveling path is controlled.

An autonomous traveling robot of an embodiment of the disclosure includes (but not limited to) a moving mechanism, a memory, and a processor. The memory is used to store a program code. The processor is coupled to the moving mechanism and the memory. The processor is used to load the program code to obtain a target area, decide a traveling path by a safety distance, and control the moving mechanism to move by the traveling path. The traveling path is at least at the safety distance from an edge of the target area.

Based on the above, according to the path planning method and the autonomous traveling robot of the embodiments of the disclosure, the traveling path at the specific safety distance from the edge of the target area may be set. In this way, the operating efficiency can be improved and resources can be saved. For applications such as the UVC sterilizing robot, collisions can be prevented or reduced, while maintaining the sterilizing efficiency.

In order for the features and advantages of the disclosure to be more comprehensible, the following specific embodiments are described in detail in conjunction with the drawings.

DETAILED DESCRIPTION OF DISCLOSED EMBODIMENTS

Figure 1:
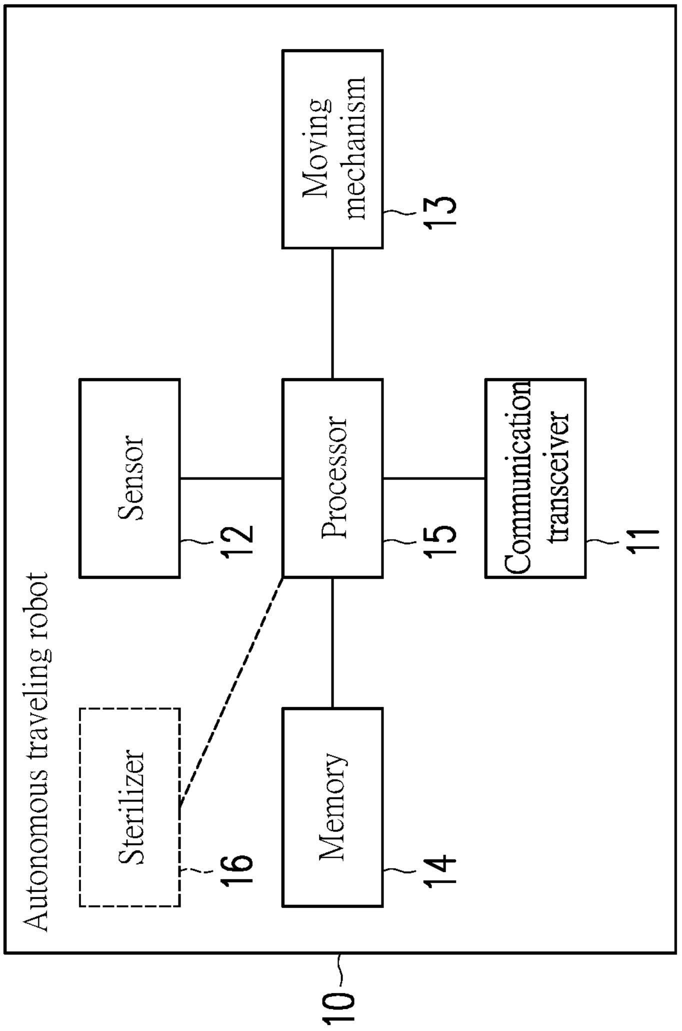
FIG. 1 is a block diagram of elements of an autonomous traveling robot according to an embodiment of the disclosure.

FIG. 1 is a block diagram of elements of an autonomous traveling robot 10 according to an embodiment of the disclosure. Please refer to FIG. 1. The autonomous traveling robot 10 includes (but not limited to) a communication transceiver 11, a sensor 12, a moving mechanism 13, a memory 14, and a processor 15.

The communication transceiver 11 may be a transceiver circuit supporting mobile network, Bluetooth, Wi-Fi, or other wireless communication technologies. In an embodiment, the communication transceiver 11 is used to transmit or receive data with an external device (for example, a server, a router, or a mobile phone) via a network.

The sensor 12 may be an optical radar, a camera, an ultrasonic transceiver, a time of flight (ToF) camera, a depth sensor, or a combination thereof. In an embodiment, sensing data (for example, the intensity of multiple elements in a sensing matrix) of the sensor 12 may be used to decide the position and the orientation of an object.

In addition, the sensor 12 may be an accelerometer, a gyroscope, an electronic compass, an inertial sensor, or a combination thereof. In an embodiment, sensing data (for example, the acceleration, the direction, or the angle) of the sensor 12 may be used to decide the position and/or the posture of the autonomous traveling robot 10 and may be used by a navigation system of the autonomous traveling robot 10.

The moving mechanism 13 may include a power unit (for example, a motor or an engine), a transmission system (for example, a transmission shaft or a variable speed shaft), and a drive wheel (for example, a wheel or a track). In an embodiment, the purpose of changing the position (moving) can be achieved through controlling the driving of an actuator (for example, the motor or the engine) of the moving mechanism 13.

The memory 14 may be any type of fixed or removable random access memory (RAM), read only memory (ROM), flash memory, hard disk drive (HDD), solid-state drive (SSD), or similar elements. In an embodiment, the memory 14 is used to store a program code, a software module, a configuration, data, or a file (for example, sensing data, map data, object data, distance, position, etc.), which will be described in detail in subsequent embodiments.

The processor 15 is coupled to the communication transceiver 11, the sensor 12, the moving mechanism 13, and the memory 14. The processor 15 may also be a central processing unit (CPU), a graphics processing unit (GPU), other programmable general purpose or specific purpose microprocessors, digital signal processors (DSP), programmable controllers, field programmable gate arrays (FPGA), application-specific integrated circuits (ASIC), neural network accelerators, other similar elements, or a combination of the above elements. In an embodiment, the processor 15 is used to execute all or some operations of the autonomous traveling robot 10 and may load and execute each software module, file, and data recorded in the memory 14.

In an embodiment, the autonomous traveling robot 10 further includes a sterilizer 16. That is, the autonomous traveling robot 10 is provided with the sterilizer 16. The sterilizer 16 is coupled to the processor 15. The sterilizer 16 may be a UVC sterilizing lamp, an alcohol spray gun, or a vector mosquito sterilizing sprayer. However, in other embodiments, for different application scenarios, the autonomous traveling robot 10 may also be equipped with a cleaning system, a transportation mechanism, a meal ordering system, or a monitoring system.

In an embodiment, the autonomous traveling robot 10 further includes a display (not shown). The display is coupled to the processor 15. The display is used to present a user interface or information.

In an embodiment, the autonomous traveling robot 10 further includes a light source (not shown). The light source is coupled to the processor 15. The light source may be an LED or a light bulb.

Figure 2:
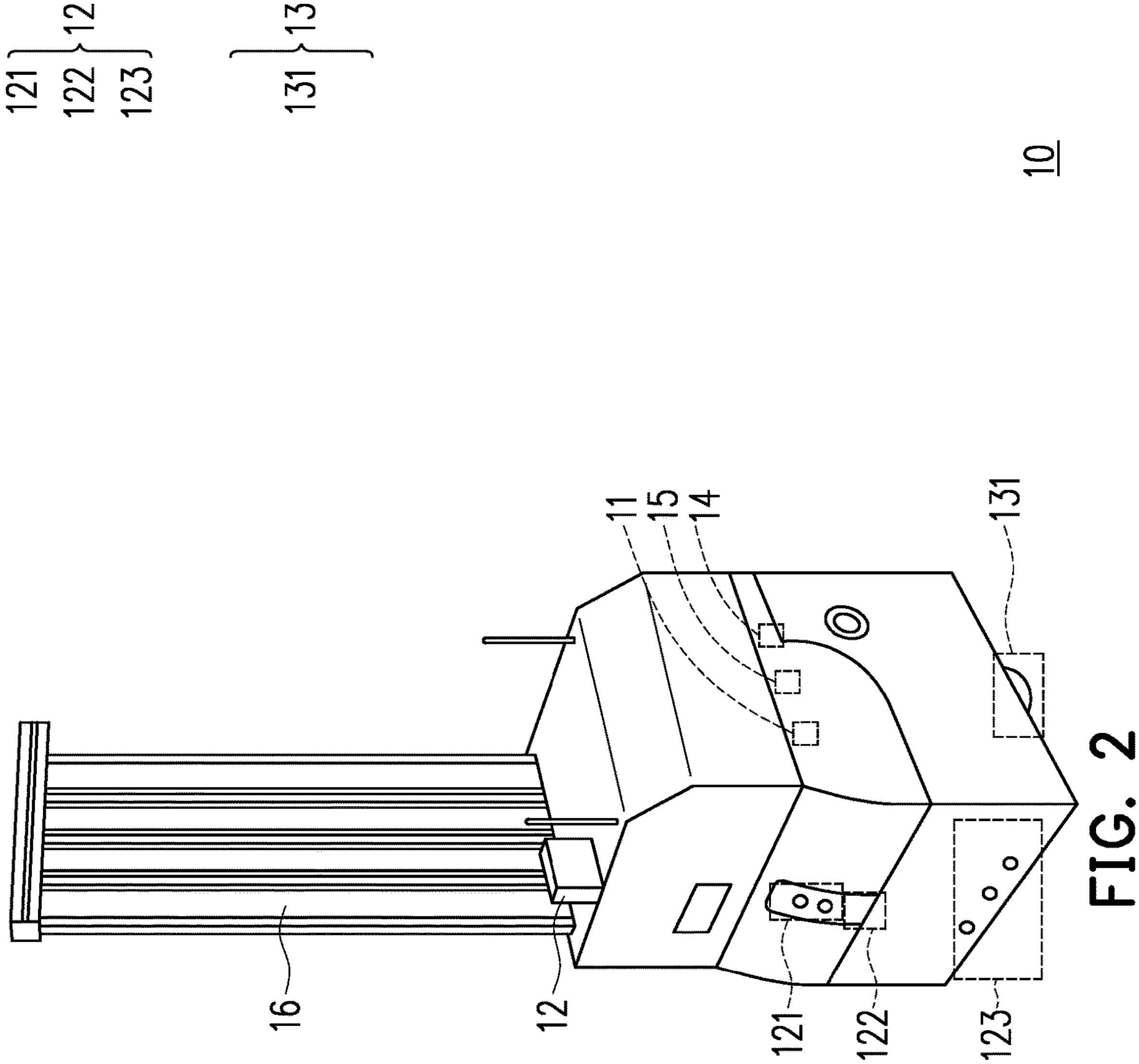
FIG. 2 is a perspective view of an autonomous traveling robot according to an embodiment of the disclosure.

In an embodiment, multiple elements of the autonomous traveling robot 10 are integrated. For example, FIG. 2 is a perspective view of an autonomous traveling robot 10 according to an embodiment of the disclosure. Please refer to FIG. 2. The sensor 12 of the autonomous traveling robot 10 includes a camera 121, an optical radar 122, and an ultrasonic transceiver 123. The camera 121, the optical radar 122, and the ultrasonic transceiver 123 are disposed on a side of the body of the autonomous traveling robot 10. The moving mechanism 13 includes a wheel 131. The communication transceiver 11, the memory 14, and the processor 15 are disposed inside the body of the autonomous traveling robot 10. In addition, the sterilizer 16 is disposed on a top side of the body of the autonomous traveling robot 10.

Figure 3A:
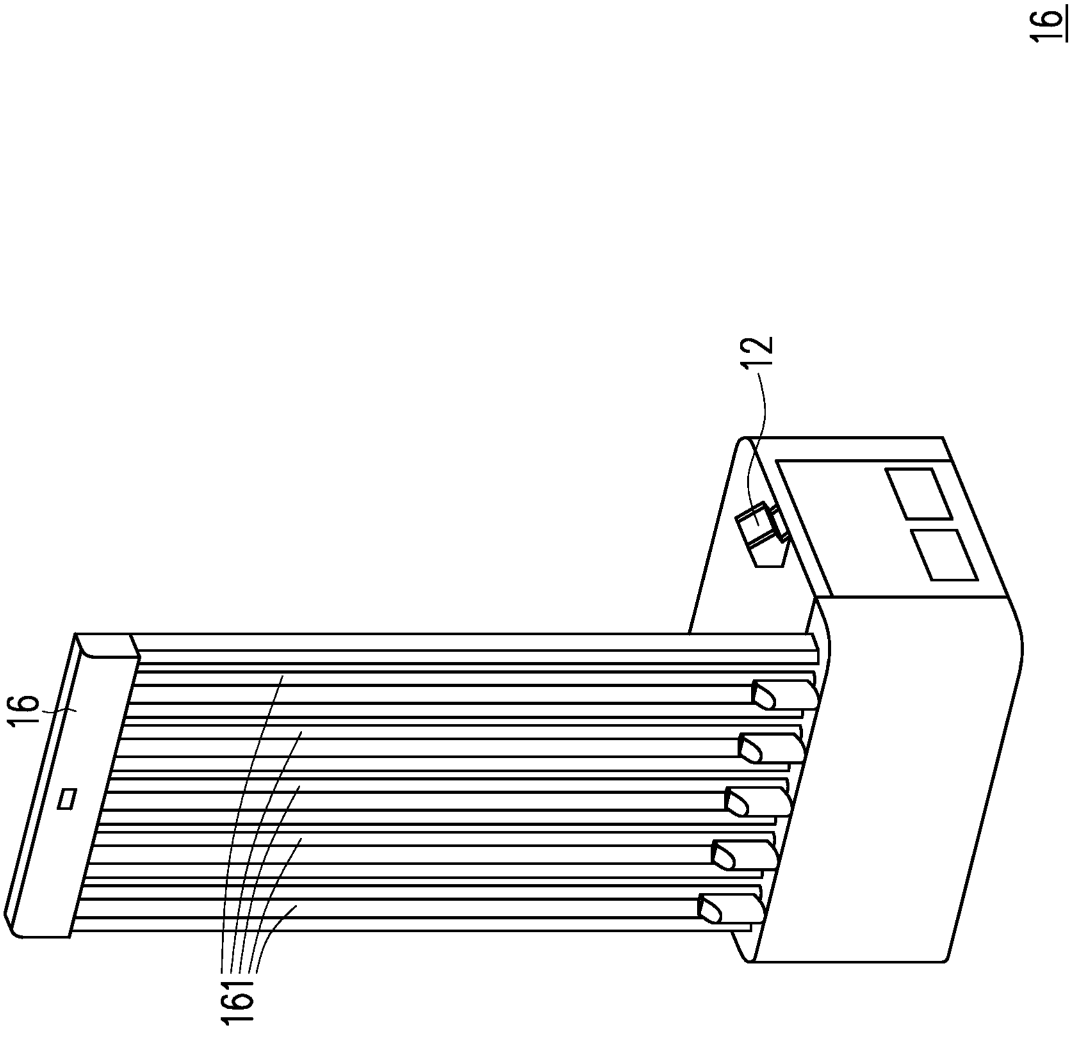
FIG. 3A is a perspective view of a sterilizer according to an embodiment of the disclosure.

FIG. 3A is a perspective view of a sterilizer 16 according to an embodiment of the disclosure. Please refer to FIG. 3A. The sterilizer 16 is exemplified as a UVC sterilizing lamp. The sterilizing lamp includes multiple light bars 161 for emitting UVC.

Figure 3B:
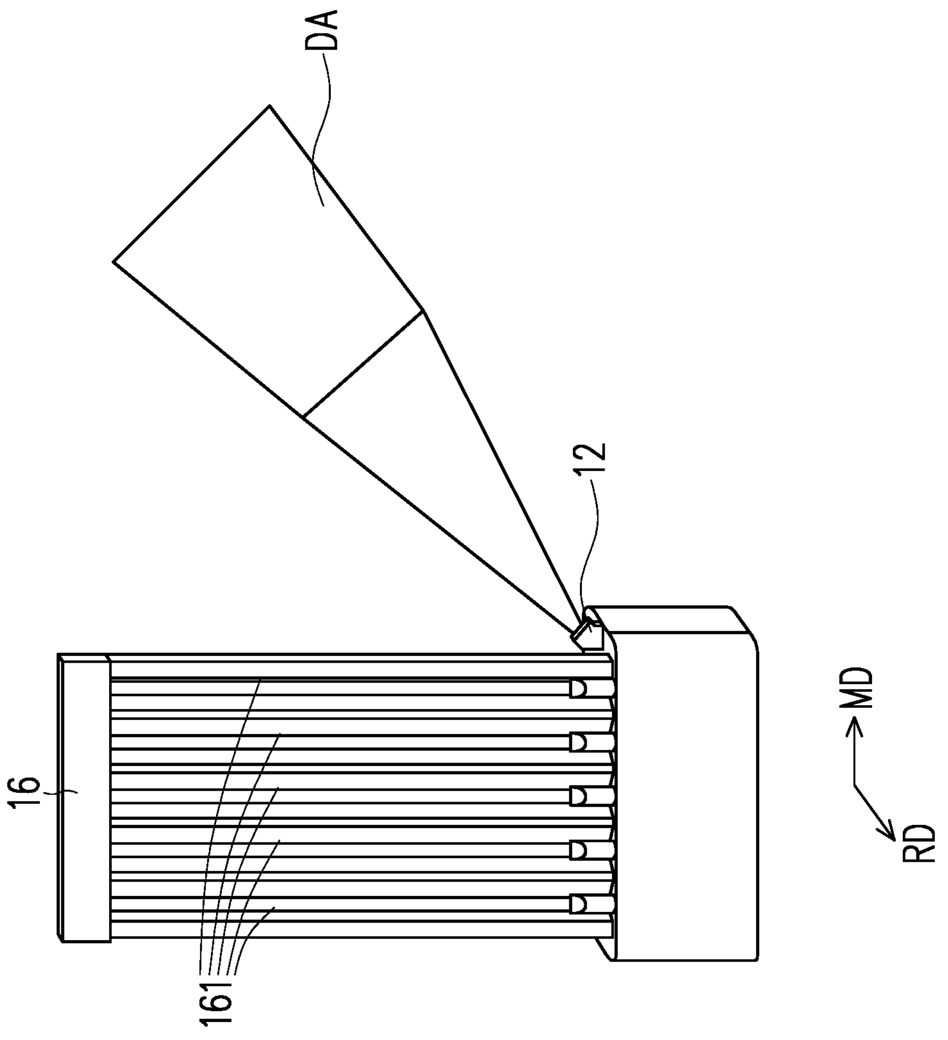
FIG. 3B and FIG. 3C are schematic views of a scanning range of a sterilizer and a sensor according to an embodiment of the disclosure.
Figure 3C:
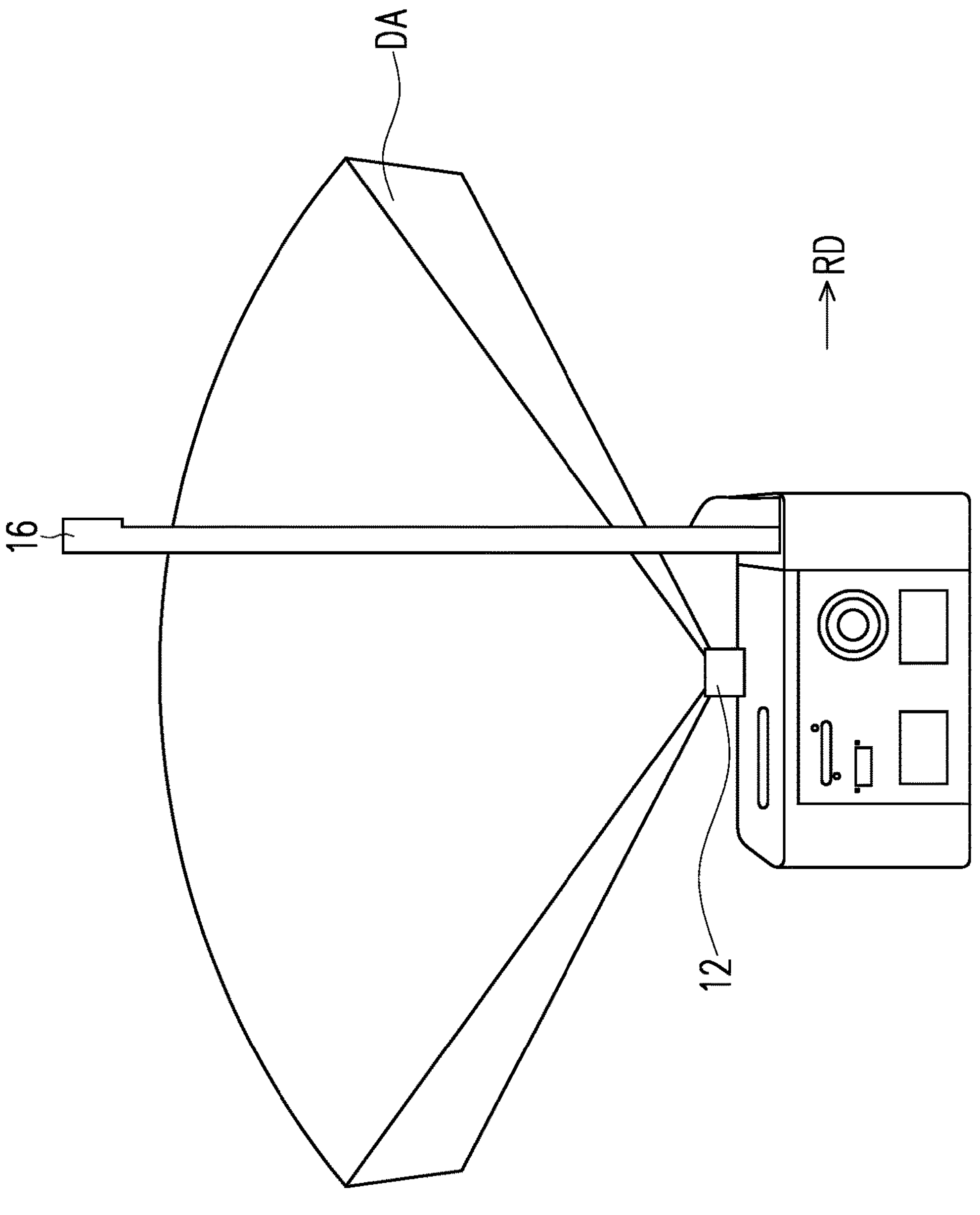

FIG. 3B and FIG. 3C are schematic views of a scanning range DA of the sterilizer 16 and the sensor 12 according to an embodiment of the disclosure. Please refer to FIG. 3B. The sensor 12 of, for example, a camera, an optical radar, or an ultrasonic transceiver scans toward a traveling direction MD (for example, the right of the drawing) of the autonomous traveling robot 10. Assuming that the autonomous traveling robot 10 advances toward the traveling direction MD, the scanning range DA of the sensor 12 is located in a specific range in front of the autonomous traveling robot 10. On the other hand, a lamp tube of the sterilizer 16 irradiates toward an irradiation direction RD (for example, the front of the drawing). Please refer to FIG. 3C. The scanning range DA is fan-shaped and the irradiation direction RD is toward the right of the drawing. In other words, when the autonomous traveling robot 10 advances toward the traveling direction MD, the sterilizer 16 sterilizes toward the right.

It should be noted that the hardware structures shown in FIG. 2 and FIG. 3A to FIG. 3C are only for illustration, and there may be other changes in other embodiments.

In order to facilitate the understanding of the operation process of the embodiment of the disclosure, the following will illustrate the operation process of a map construction device 100 in the embodiment of the disclosure in detail with several embodiments. Hereinafter, the method of the embodiment of the disclosure will be described in combination with each device and an element or a module thereof in the autonomous traveling robot 10.

Figure 4:
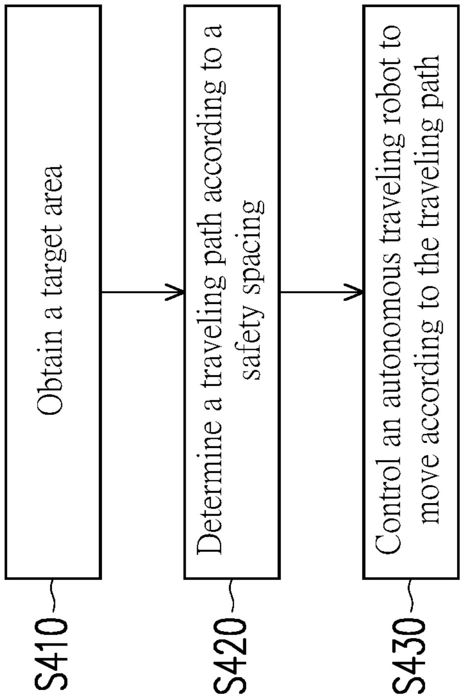
FIG. 4 is a flowchart of a path planning method according to an embodiment of the disclosure.

FIG. 4 is a flowchart of a path planning method according to an embodiment of the disclosure. Please refer to FIG. 4. The processor 15 obtains a target area (Step S410). Specifically, according to different application requirements, the target area may be a sterilizing area, a monitoring area, a transportation area, or a cleaning area of the autonomous traveling robot 10 or an application range of other applications.

In an embodiment, the processor 15 may receive a selecting operation of a target object. The selecting operation may be an operation through an input device (for example, a touch screen or a button) and directed at the target object or an operation received from an external device (for example, a mobile phone, a tablet computer, or a desktop computer) through the communication transceiver 11 and directed at the target object. The target object may be a machine, a production line, a furniture, a home appliance, a person, or a building structure. In an embodiment, the target object is the sterilizer 16 or a target of a sterilizing operation. In other embodiments, the target object may be a target of other operations.

The processor 15 may define an edge of the target area by an outline of the target object. The outline of the target object is, for example, an edge defined by a top view angle. The processor 15 may define the edge of the target area to be the same or roughly the same as the outline of the target object.

Figure 5:
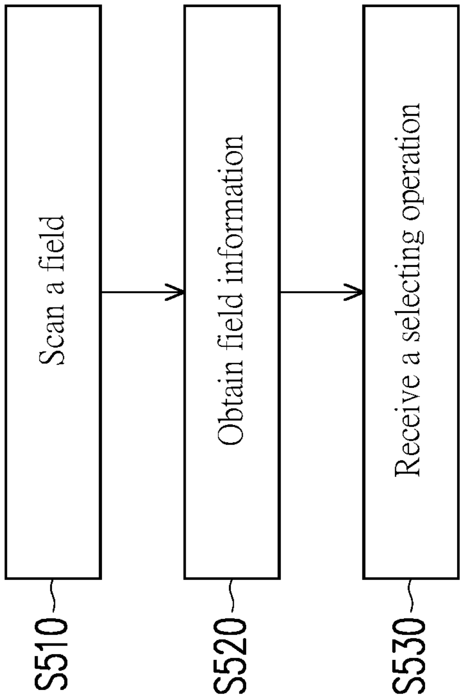
FIG. 5 is a flowchart of deciding a target area according to an embodiment of the disclosure.

For example, FIG. 5 is a flowchart of deciding a target area according to an embodiment of the disclosure. Please refer to FIG. 5. The autonomous traveling robot 10 may scan a field (Step S510). For example, the processor 15 may drive the moving mechanism 13 to move and control the sensor 12 to obtain sensing data. The processor 15 may convert the sensing data into depth or distance information, and generate a two-dimensional map of the field accordingly. In other embodiments, the processor 15 may receive a two-dimensional map of the field or a plan/floor layout of the field generated by other sensors or scanners through the communication transceiver 11.

The processor 15 obtains field information (Step S520). The field information may include the positions (which may be converted into coordinates) and the face/heading angles of a structure and an object on the map. The processor 15 may decide the type of the structure and/or the target object according to an image recognition technology or a marking result.

The processor 15 may receive the selecting operation (Step S530). The selecting operation is received through an internal or external input device and is an operation of selecting an object on the map. That is, the selecting operation is used to use a selected object as the target object.

In an embodiment, the processor 15 may provide a user interface, such as displaying the user interface through an internal or external display. The user interface may present the two-dimensional map of the field, such as the two-dimensional map or the plan layout generated by scanning.

The processor 15 may receive an editing operation on the two-dimensional map through the internal or external input device. The editing operation includes adding a target node of the target area. The processor 15 may define the edge of the target area by the editing operation. The target node is located at the edge of the target area. Multiple adjacently connected target nodes form the edge/range of the target area. For example, the target area is a polygon and the target node is a junction point/place of any two sides of the polygon. As another example, the target area is a line segment and the target node is a relay point, a start point, or an end point on the line segment. However, the embodiment of the disclosure does not limit the shape of the target area.

Please refer to FIG. 4. The processor 15 decides a traveling path by a safety distance (Step S420). Specifically, the traveling path is at least at the safety distance from the edge of the target area. That is, the shortest distance between the traveling path and the edge of the target area is the safety distance. However, in some application scenarios, the distance between the traveling path and the edge of the target area may still be adjusted according to requirements. In an embodiment, the processor 15 may define the safety distance by an application range of the sterilizer 16. In other embodiments, the safety distance may be related to the application range of other operations or other predetermined distances.

In an embodiment, the processor 15 may define the target node on the edge of the target area. In other words, the target node is located on the edge of the target area. The target node is, for example, the intersection point of two sides of the polygon or any point on the line segment.

The processor 15 may extend the safety distance outwardly from the target node away from the target area for an extension node being generated. For example, the extension node is located on the normal of the edge of the target area on the target node and is at the safety distance from the target node. The processor 15 may use the extension node as a path node in the traveling path.

In an embodiment, the shape of the target area is exemplified as a polygon. The target area includes a first side and a second side, and the target node is located at a junction (that is, an intersection point) of the first side and the second side. The processor 15 may extend an extension distance from the target node along the first side for a first node being generated. That is, the first node is at a distance of the extension distance from the target node, and there is a first calculation included angle (θa) between a connection line of the first node and the target node and the second side. Similarly, the processor 15 extends the same extension distance from the target node along the second side for a second node being generated, and there is a second calculation included angle (θb) between a connection line of the second node and the target node and the first side. Since the first calculation included angle (θa) and the second calculation included angle (θa) are diagonally related, the first calculation included angle (θa) is equal to the second calculation included angle (θa), hereinafter referred to as a calculation included angle (θ). In other words, the second node is at a distance of the extension distance from the target node. The projection amount of the extension distance on an imaginary line corresponding to the safety distance is the shortest distance. For example, the normal of the first side or the second side is used as the imaginary line.

The processor 15 may define a parallelogram by a first extension segment from the first node to the target node, a second extension segment from the second node to the target node, and a first included angle (θx) between the first extension segment and the second extension segment, and define a second path node in the traveling path by a vertex of the parallelogram. The first node, the second node, the target node, and the second path node are the vertices of the parallelogram. Therefore, if the first extension segment, the second extension segment, and the first included angle between the two extension segments are known, the processor 15 may decide another vertex (that is, an intersection point/a junction of the two opposite sides, which may be used as the second path node) in the parallelogram opposite to the target node based on the symmetry property of the parallelogram to be defined as a path node in the traveling path accordingly. In addition, the sum of the first included angle (θx) between the first extension segment and the second extension segment and the first calculation included angle (θa) between the connection line of the first node and the target node and the second side is 180 degrees. In other words, the sum of the first included angle (θx) between the first extension segment and the second extension segment and the second calculation included angle (θb) between the connection line of the second node and the target node and the first side is also 180 degrees. Therefore, the first included angle (θx) and the calculation included angle (θ) are complementary angles.

In an embodiment, the processor 15 may define the second path node by the sum of a first vector from the target node to the first node and a second vector from the target node to the second node respectively added to the coordinates of the target node. For the parallelogram, the second path node is an intersection point located on the opposite angle of the target node. The vector represents that there is a directional displacement on the two-dimensional coordinate system. Therefore, the second path node may be reached by displacing starting from the target node along the first vector and the second vector.

In an embodiment, when the coordinates of the three vertices of the parallelogram are known, the processor 15 may also calculate the unknown fourth vertex (that is, the second path node) by using the property of diagonals.

In another embodiment, the second path node may also be any point on the opposite side of the first side or the second side of the parallelogram.

Figure 6:
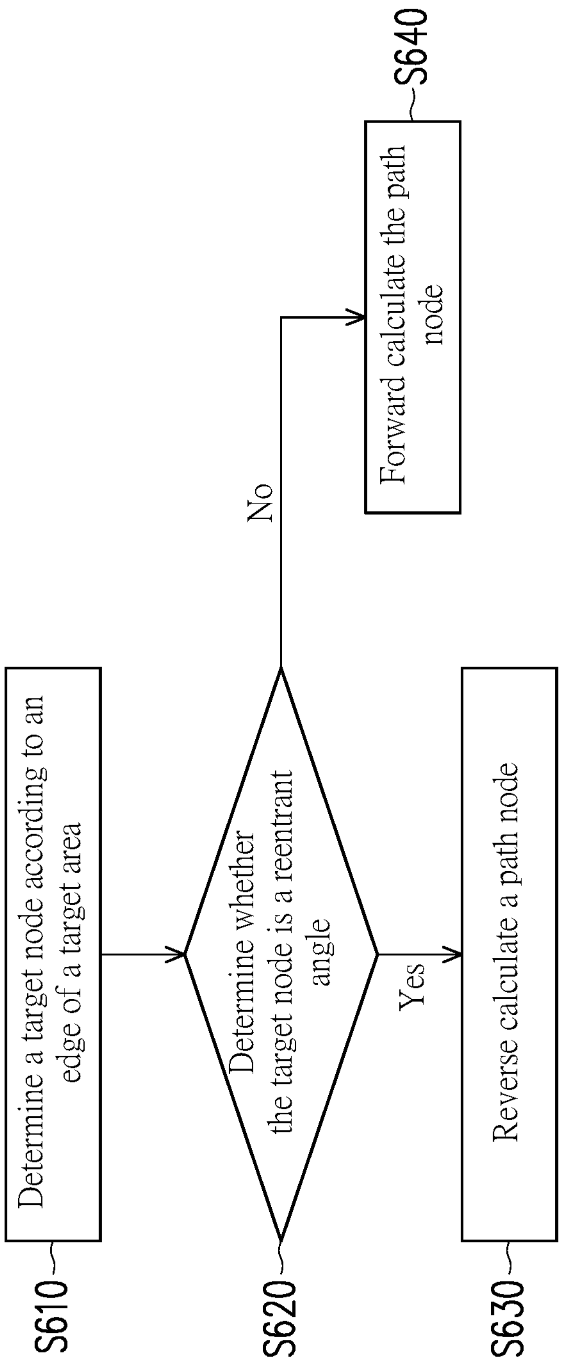
FIG. 6 is a flowchart of deciding a node according to an embodiment of the disclosure.

FIG. 6 is a flowchart of deciding a node according to an embodiment of the disclosure. Please refer to FIG. 6. The processor 15 may decide the target node according to the edge of the target area (Step S610). That is, the target node is located on the edge of the target area. The shape of the target area is exemplified as a polygon, and the target node may be an intersection point of the first side and the second side.

The processor 15 may decide whether an included angle corresponding to the target node outside the target area is a reentrant angle (Step S620). For example, the processor 15 may define a second included angle (θy) corresponding to the target node at a junction of the first side and the second side in the target area and may decide whether a third included angle (θz) corresponding to the target node at the junction of the first side and the second side outside the target area is a reentrant angle. The sum of the second included angle and the third included angle is 360 degrees. The reentrant angle means that an included angle (hereinafter referred to as an interior angle) in the target area is greater than 180 degrees and an included angle (hereinafter referred to as an exterior angle) outside the target area is less than 180 degrees, and a salient angle means that an included angle (an interior angle) in the target area is less than 180 degrees and an included angle (an exterior angle) outside the target area is greater than 180 degrees. As such, it can be seen that the third included angle is equal to the exterior angle corresponding to the target node.

The processor 15 may decide whether the outer product of the first vector from the target node to the first node and the second vector from the target node to the second node has a positive value. The outer product is the normal vector of a plane where the first vector and the second vector are located. Taking the right-hand rule as an example, the index finger of the right hand points to the direction of the first vector and the middle finger points to the direction of the second vector, so the direction of the thumb is the direction of the outer product. In response to the outer product having the positive value (that is, a value greater than zero), the processor 15 may decide that the third included angle is a reentrant angle. On the other hand, in response to the outer product having a negative value (that is, a value less than zero), the processor 15 may decide that the third included angle is not a reentrant angle (that is, a salient angle).

Since the extension distances from the target node respectively to the first and second nodes are the projection amounts respectively corresponding to the first side and the second side, the reentrant angle and the salient angle need to be considered for the extension distances. In response to the third included angle corresponding to the target node at the junction of the first side and the second side outside the target area being a reentrant angle, $x=-d/\sin(\theta)$, where x is the extension distance, d is the safety distance, and θ is the calculation included angle. On the other hand, in response to the third included angle corresponding to the target node at the junction of the first side and the second side outside the target area not being a reentrant angle, $x=d/\sin(\theta)$.

In response to the third included angle being a reentrant angle, the processor 15 may reverse calculate the second path node (Step S630). The reverse calculation refers to the case where the outer product has a positive value, and $x=-d/\sin(\theta)$ may be used to decide the extension distance x. In response to the third included angle not being a reentrant angle (for example, a salient angle), the processor 15 may forward calculate the second path node (Step S640). The forward calculation refers to the case where the outer product has a negative value, and $x=d/\sin(\theta)$ may be used to decide the extension distance x.

Figure 7A:
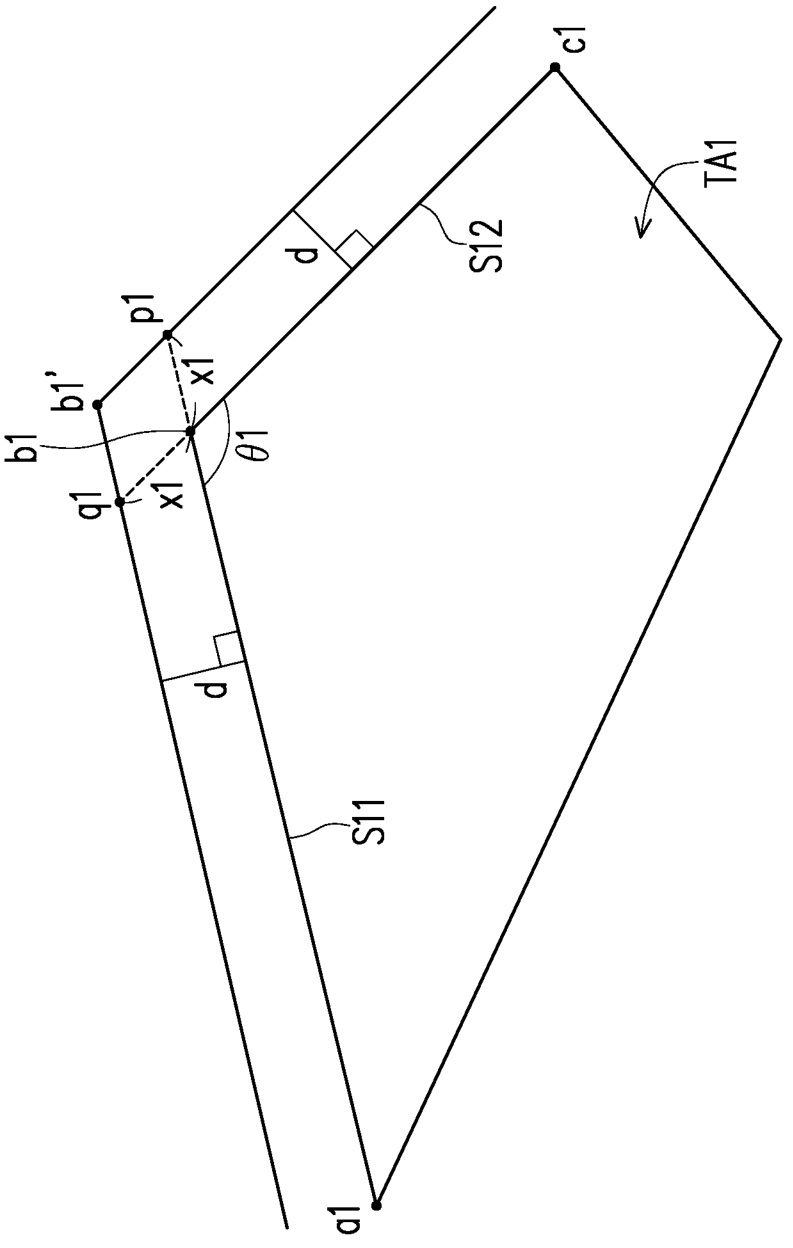
FIG. 7A is a schematic view of deciding a path node of a salient angle according to an embodiment of the disclosure.
Figure 7B:
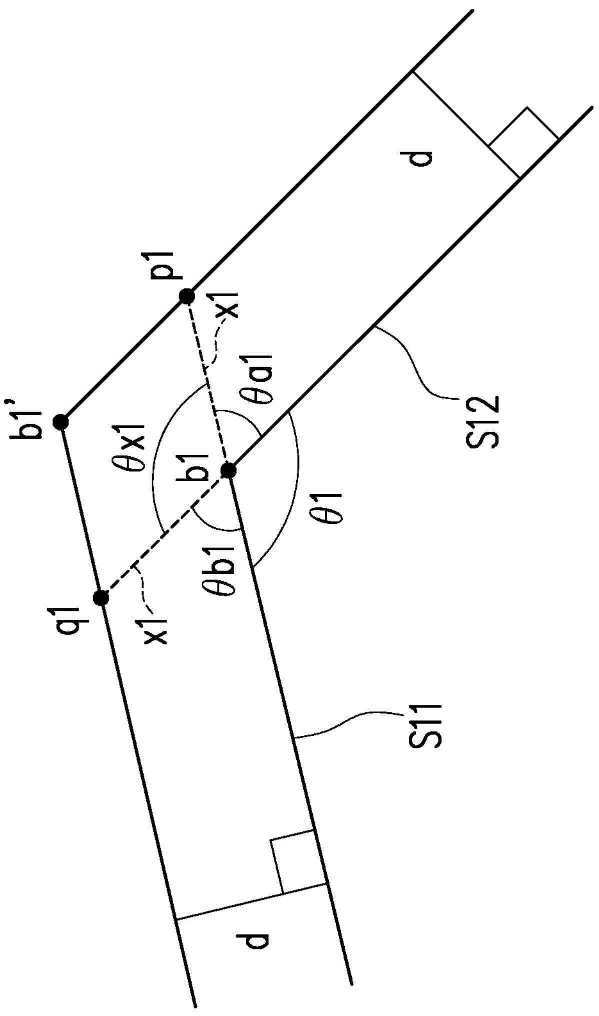
FIG. 7B is a partially enlarged view of FIG. 7A.

For example, FIG. 7A is a schematic view of deciding a path node of a salient angle according to an embodiment of the disclosure, and FIG. 7B is a partially enlarged view of FIG. 7A. Please refer to FIG. 7A. Target nodes a1, b1, and c1 of a target area TA1 are taken as an example. Since an interior angle (the second included angle) θ1 of ∠a1b1c1 is less than 180 degrees, an exterior angle (the third included angle) corresponding to ∠a1b1c1 is a salient angle, so an extension distance $x1=d/\sin(\theta)$.

Please refer to FIG. 7B. There is a first calculation included angle (θa1) between an extension line of a first side S11 formed by the target node b1 along the target nodes a1 and b1 and a second side S12 formed by the target nodes b1 and c1, and an intersection point where the first side S11 intersects with a ray parallel to the second side S12 at a distance of a safety distance d is a first node p1 (which is also a path node in the traveling path). The distance between the first node p1 and the target node b1 is x1, and $x1=d/\sin(\theta a1)$. There is a second calculation included angle (θb1) between an extension line of the second side S12 formed by the target nodes b1 and c1 and the first side S11, and an intersection point where the second side S12 intersects with a ray parallel to the first side S11 at a distance of the safety distance d is a second node q1 (which is also a path node in the traveling path). The distance between the second node q1 and the target node b1 is x1, and $x1=d/\sin(\theta b1)$.

The processor 15 may define a parallelogram by a first extension segment from the first node p1 to the target node b1, a second extension segment from the second node q1 to the target node b1, and a first included angle (θx1) between the first extension segment and the second extension segment. A new point b1 may be obtained by adding the sum of the b1p1 vector and the b1q1 vector to the coordinates of the target node b1 and is expressed as b1' (that is, the second path node).

Figure 8A:
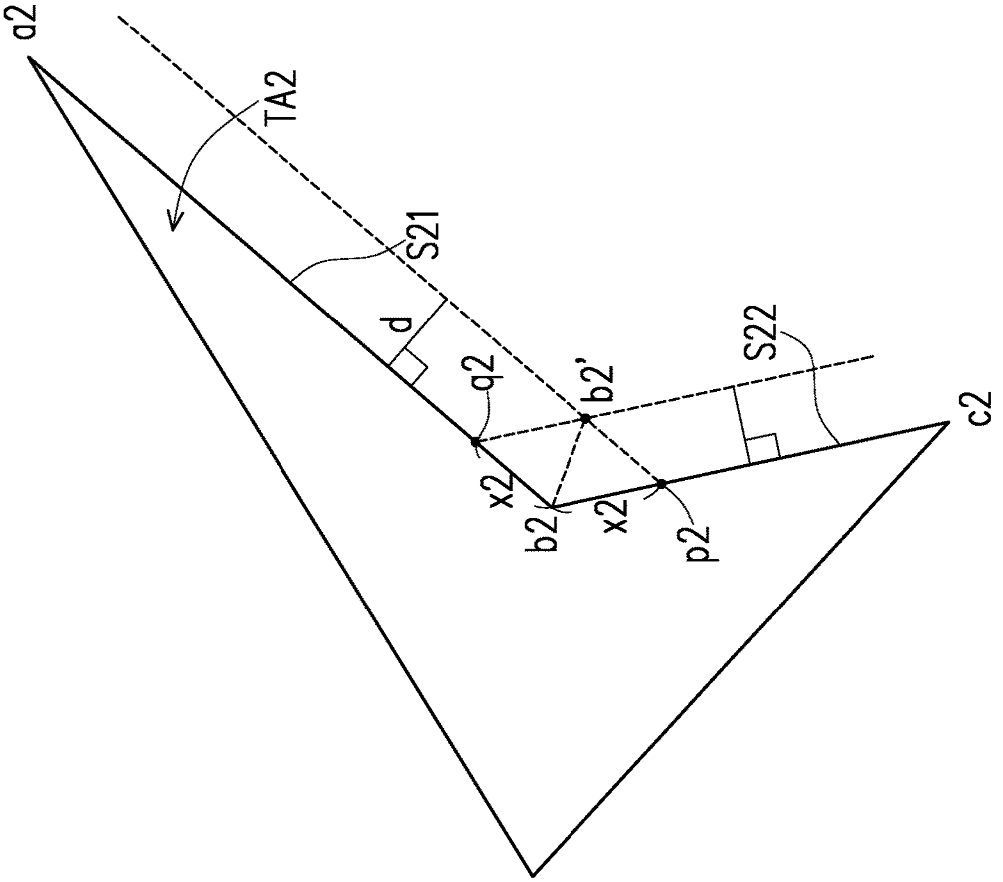
FIG. 8A is a schematic view of deciding a path node of a reentrant angle according to an embodiment of the disclosure.
Figure 8B:
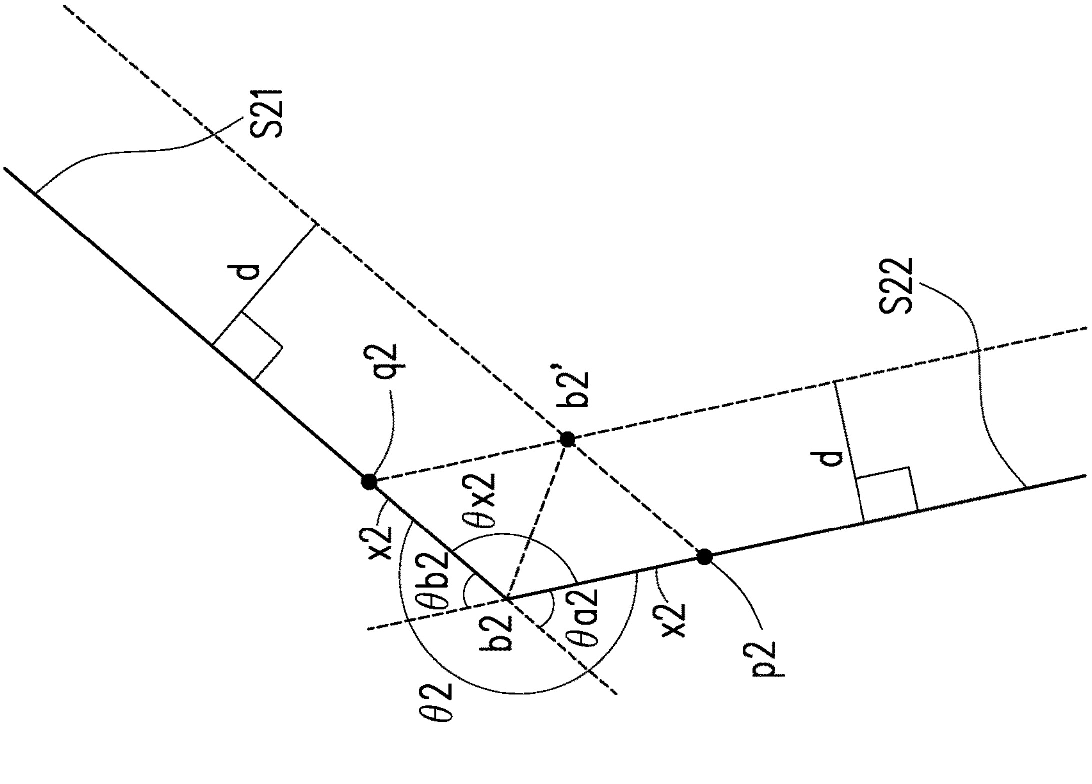
FIG. 8B is a partially enlarged view of FIG. 8A.

FIG. 8A is a schematic view of deciding a path node of a reentrant angle according to an embodiment of the disclosure, and FIG. 8B is a partially enlarged view of FIG. 8A. Please refer to FIG. 8A. Target nodes a2, b2, and c2 of a target area TA2 are taken as an example. Please refer to FIG. 8B. Since an interior angle (the second included angle) θ2 of ∠a2b2c2 is greater than 180 degrees, an exterior angle (the third included angle, that is, the first included angle θx2) corresponding to ∠a2b2c2 is a reentrant angle, and an extension distance $x2=-d/\sin(\theta)$. There is a first calculation included angle (θa2) between an extension line of a first side S21 formed by the target node b2 along the target nodes a2 and b2 and a second side S22 formed by the target nodes b2 and c2, and there is a first node q2 on the first side S21 at a distance of the extension distance x2 from the target node b2. Here, the extension distance $x2=-d/\sin(\theta a2)$. There is a second calculation included angle (θb2) between an extension line of the target node b2 along the second side S22 and the first side S21, and there is a second node p2 on the first side S21 at a distance of the extension distance x2 from the target node b2. Here, the extension distance $x2=-d/\sin(\theta b2)$.

The processor 15 may define a parallelogram by a first extension segment from the first node q2 to the target node b2, a second extension segment from the second node p2 to the target node b2, and a first included angle (θx2) between the first extension segment and the second extension segment. A new point b2 may be obtained by adding the sum of the b2p2 vector and the b2q2 vector to the coordinates of the target node b2 and is expressed as b2' (that is, the second path node).

In an embodiment, there are multiple path nodes on the traveling path, and the processor 15 may define the sequence of the path nodes by the application orientation of the sterilizer 16. Taking the sterilizer 16 shown in FIG. 3B and FIG. 3C as an example, the sterilizer 16 irradiates or performs the sterilizing operation toward the right. Therefore, the processor 15 may sort the path nodes according to the clockwise direction. For example, if the value of the outer product of two vectors extending from a certain path node is greater than zero, the processor 15 defines the path node as counterclockwise, which needs to be further corrected to the clockwise sequence. On the contrary (that is, when the value of the outer product is less than zero), the correction of the sequence may be ignored. Taking [‘A’, ‘B’, 'C', 'D', 'E'] as an example, the converted sequence becomes ['A', 'E', 'D', 'C', 'B']. In another embodiment, the processor 15 may correct the sequence of the target nodes, and reference may be made to the corrected sequence of the target nodes for the sequence of the path nodes.

On the other hand, in response to the sterilizer 16 performing the sterilizing operation toward the left, the processor 15 may sort the path nodes according to the counter-clockwise direction. However, there may also be other variations in the sequence of the path nodes.

Please refer to FIG. 4. The processor 15 controls the moving mechanism 13 to move by the traveling path (Step S430). For example, the moving mechanism 13 drives the body of the autonomous traveling robot 10 to sequentially reach multiple path nodes in the traveling path. For another example, the moving mechanism 13 directly travels according to the trajectory of the traveling path.

Figure 9:
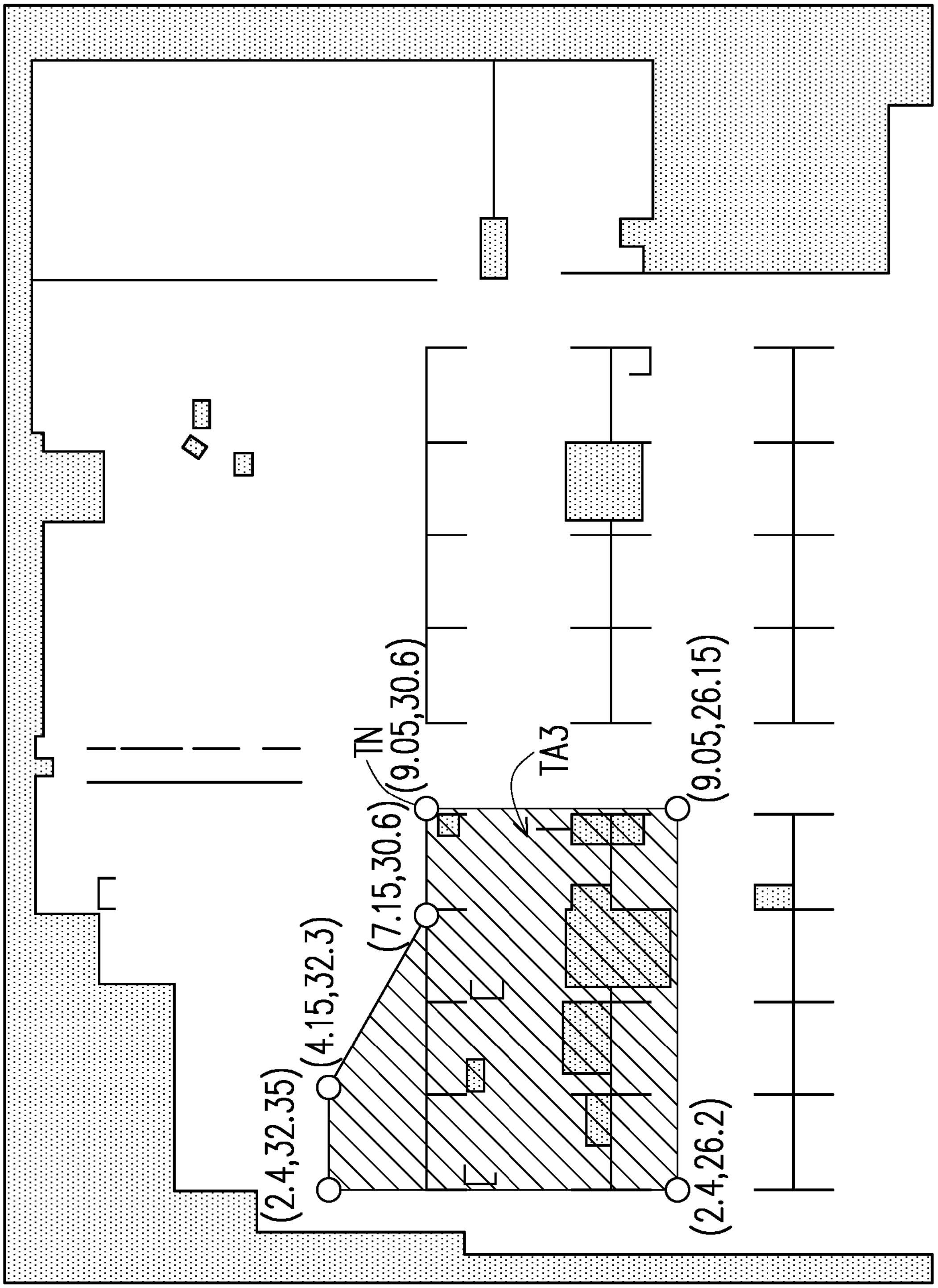
FIG. 9 is a schematic view of a target area in a two-dimensional map according to an embodiment of the disclosure.

For example, FIG. 9 is a schematic view of a target area TA3 in a two-dimensional map according to an embodiment of the disclosure. Please refer to FIG. 9. Taking the target node with the coordinates (7.15, 30.6) as an example, the processor 15 may define that three target nodes TN [previous target node, current target node, next target node]=[(4.15, 32.3), (7.15, 30.6), (9.05, 30.6)], and may calculate whether an interior angle formed by a connection line of the three target nodes in the target area is greater than 180 degrees, that is, whether an exterior angle is a reentrant angle.

It is assumed that the safety distance d=0.7 (meter). If the first node and the second node located in the traveling path are to be calculated, the extension distance may be first decided as 1.42 (meters). The outer product corresponding to the target node TN located at the coordinates (7.15, 30.6) is greater than zero. For the right-hand rule, the thumb points upward and the remaining four fingers rotate counterclockwise. On the premise that all vertices of the target area TA3 are sorted clockwise, if an angle is calculated as counterclockwise (that is, the outer product is greater than zero), it means that the angle is a reentrant angle. In response thereto, an exterior angle corresponding to the vertex at the coordinates (7.15, 30.6) is a reentrant angle.

Since the exterior angle corresponding to the vertex at the coordinates (7.15, 30.6) is a reentrant angle, during the process of calculating the first node and the second node, $x=-d/\sin(\theta)$ is used to correct the directions of a first vector (that is, a vector from the target node TN to the first node) and a second vector (that is, a vector from the target node TN to the second node). The first node is located at the coordinates (5.91, 31.3) and the second node is located at the coordinates (8.57, 30.6).

Figure 10:
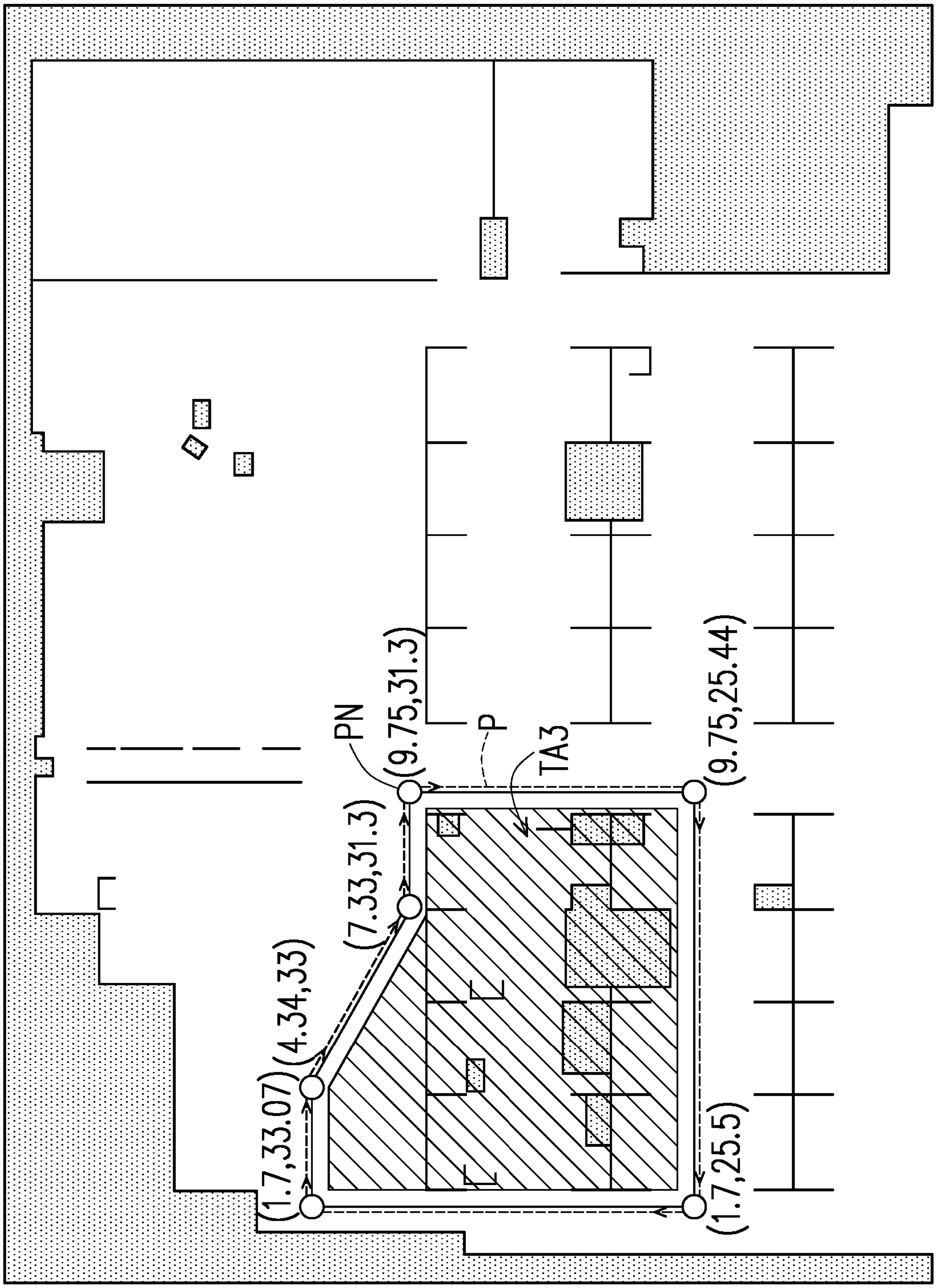
FIG. 10 is a schematic view of a traveling path obtained according to the target area of FIG. 9.

FIG. 10 is a schematic view of a traveling path P (shown by dotted lines) obtained according to the target area of FIG. 9. Please refer to FIG. 10. Knowing the coordinates of the three vertices of the parallelogram, the processor 15 may obtain the coordinates (7.33, 31.3) of the fourth vertex (that is, a second path node PN of the traveling path P).

Please refer to FIG. 9 and FIG. 10. By analogy, the coordinates (9.75, 31.3) of the second path node PN may be obtained from the target node located at the coordinates (9.05, 30.6); the coordinates (9.75, 25.44) of the second path node PN may be obtained from the target node at the coordinates (9.05, 26.15); the coordinates (1.7, 25.5) of the second path node PN may be obtained from the target node at the coordinates (2.4, 26.2); the coordinates (1.7, 33.07) of the second path node PN may be obtained from the target node at the coordinates (2.4, 32.35); and the coordinates (4.34, 33) of the second path node PN may be obtained from the target node at the coordinates (4.15, 32.3).

The moving mechanism 13 may sequentially reach each second path node PN. Along the traveling path P, the shortest distance between the autonomous traveling robot 1 and an edge of the target area TA3 is 0.7 (meter).

On the other hand, during the process of the moving mechanism 13 moving, the processor 15 may activate the sterilizer 16 to perform the sterilizing operation. Alternatively, according to different application requirements, the autonomous traveling robot 10 may perform other operations, such as monitoring, cleaning, or transportation operations.

In summary, in the path planning method and the autonomous traveling robot of the embodiments of the disclosure, the shape of the generated traveling path is similar to the shape of the target area, and the traveling path is ensured to be at the safety distance from the edge of the target area. In addition, for the target area of the polygon, no matter whether the corresponding exterior angle located at the vertex is a salient angle or a reentrant angle, the corresponding path node may be located outside the target area. In this way, a route that maximizes the operation efficiency of the autonomous traveling robot can be obtained.

Although the disclosure has been disclosed in the above embodiments, the embodiments are not intended to limit the disclosure. Persons skilled in the art may make some changes and modifications without departing from the spirit and scope of the disclosure. Therefore, the protection scope of the disclosure shall be defined by the appended claims.

What is claimed is:

1. A path planning method, comprising:

obtaining a target area;

deciding a traveling path by a safety distance, wherein the traveling path is at least at the safety distance from an edge of the target area, and the step of deciding the traveling path by the safety distance comprises:

defining a target node located on the edge of the target area, defining a shortest distance from the target node located on the edge of the target area to the traveling path as the safety distance;

extending the safety distance outwardly from the target node away from the target area for an extension node being generated, wherein the extension node is located on a normal line of the edge of the target area on the target node, and the extension node is located at the shortest distance from the target node, the target area comprises a first side, and the step of extending the safety distance outwardly from the target node comprises: extending an extension distance from the target node along the first side for a first node being generated and defining the extension node based on the first node, wherein a projection amount of the extension distance on the normal of the first side corresponding to the safety distance is the shortest distance; and using the extension node as a path node in the traveling path; and controlling an autonomous traveling robot being moved by the traveling path, wherein the target area further comprises a second side, the target node is located at a junction of the first side and the second side, and the path planning method further comprising:

defining a calculation included angle between the second side and a connection line of the target node and the first node;

defining a second included angle between the first side and the second side in the target area;

deciding whether a third included angle corresponding to the target node located at the junction of the first side and the second side outside the target area is a reentrant angle, wherein the step of deciding whether the third included angle is the reentrant angle comprises:

deciding whether an outer product of a first vector from the target node to the first node and a second vector from the target node to the second node has a positive value;

deciding that the third included angle is the reentrant angle in response to the outer product having the positive value; and deciding that the third included angle is not the reentrant angle in response to the outer product having a negative value, selecting, based on the determination of the outer product, a calculation mode for the extension distance associated with maintaining the safety distance from a boundary of the target area, in response to the third included angle being the reentrant angle, performing a reverse calculation of the extension node, wherein the reverse calculation refers to the case where the outer product has the positive value and $x=-d/\sin(\theta)$, where x is the extension distance, d is the safety distance, θ is the calculation included angle, wherein the extension distance x simultaneously defines a magnitude that varies as a function of θ and a direction determined by a sign of x, wherein a negative value of the extension distance defines an inward extension direction towards an interior of the target area, and wherein the extension node is generated by the reverse calculation based on the negative value of the extension distance, and in response to the third included angle not being the reentrant angle, performing a forward calculation of the extension node, wherein the forward calculation refers to the case where the outer product has the negative value and $x=d/\sin(\theta)$ is used to decide the extension distance, wherein a positive value of the extension distance defines an outward extension direction away from the boundary of the target area, and wherein the extension node is generated by the forward calculation based on the positive value of the extension distance.

2. The path planning method according to claim 1, wherein the step of extending the safety distance outwardly from the target node comprises:

extending the extension distance from the target node along the second side for a second node being generated;

defining a parallelogram by a first extension segment from the target node to the first node, a second extension segment from the target node to the second node, and a first included angle between the first extension segment and the second extension segment; and defining a second path node in the traveling path by a plurality of vertices of the parallelogram, wherein the first node, the second node, the target node, and the second path node are the plurality of vertices of the parallelogram.

3. The path planning method according to claim 2, wherein the step of defining the second path node in the traveling path comprises: defining the second path node by a sum of a first vector from the target node to the first node and a second vector from the target node to the second node respectively added to coordinates of the target node.

4. The path planning method according to claim 1, wherein the autonomous traveling robot is provided with a sterilizer and there are a plurality of path nodes on the traveling path, the path planning method further comprising:

defining a sequence of the path nodes by an application orientation of the sterilizer.

5. The path planning method according to claim 1, wherein the autonomous traveling robot is provided with a sterilizer, the path planning method further comprising:

defining the safety distance by an application range of the sterilizer.

6. The path planning method according to claim 1, wherein the step of deciding the target area comprises:

receiving a selecting operation of a target object; and defining the edge of the target area by an outline of the target object.

7. The path planning method according to claim 1, wherein the step of deciding the target area comprises:

providing a user interface, wherein the user interface presents a two-dimensional map;

receiving an editing operation on the two-dimensional map, wherein the editing operation comprises adding the target node of the target area; and defining the edge of the target area by the editing operation, wherein the target node is located at the edge of the target area.

8. An autonomous traveling robot, comprising:

a moving mechanism;

a memory, for storing a program code; and a processor, coupled to the moving mechanism and the memory, and for loading the program code to:

obtain a target area;

decide a traveling path by a safety distance, wherein the traveling path is at least at the safety distance from an edge of the target area; and control the autonomous traveling robot being moved by the traveling path, wherein the processor further executes:

defining a target node located on the edge of the target area, defining a shortest distance from the target node located on the edge of the target area to the traveling path as the safety distance;

extending the safety distance outwardly from the target node away from the target area for an extension node being generated, wherein the extension node is located on a normal line of the edge of the target area on the target node, and the extension node is located at the shortest distance from the target node, the target area comprises a first side, and the processor further executes: extending an extension distance from the target node along the first side for a first node being generated and defining the extension node based on the first node, wherein a projection amount of the extension distance on the normal of the first side corresponding to the safety distance is the shortest distance; and using the extension node as a path node in the traveling path, wherein the target area further comprises a second side, the target node is located at a junction of the first side and the second side, and the processor further executes:

defining a calculation included angle between a connection line of the target node and the first node and the second side;

defining a second included angle between the first side and the second side in the target area; deciding whether a third included angle corresponding to the target node located at the junction of the first side and the second side outside the target area is a reentrant angle, wherein the processor further executes:

deciding whether an outer product of a first vector from the target node to the first node and a second vector from the target node to the second node has a positive value;

deciding that the third included angle is the reentrant angle in response to the outer product having the positive value; and deciding that the third included angle is not the reentrant angle in response to the outer product having a negative value, selecting, based on the determination of the outer product, a calculation mode for the extension distance associated with maintaining the safety distance from a boundary of the target area, in response to the third included angle being the reentrant angle, performing a reverse calculation of the extension node, wherein the reverse calculation refers to the case where the outer product has the positive value and $x=-d/\sin(\theta)$, where x is the extension distance, d is the safety distance, θ is the calculation included angle, wherein the extension distance x simultaneously defines a magnitude that varies as a function of θ and a direction determined by a sign of x, wherein a negative value of the extension distance defines an inward extension direction towards an interior of the target area, and wherein the extension node is generated by the reverse calculation based on the negative value of the extension distance, and in response to the third included angle not being the reentrant angle, performing a forward calculation of the extension node, wherein the forward calculation refers to the case where the outer product has the negative value and $x=d/\sin(\theta)$ is used to decide the extension distance, wherein the positive value of the extension distance defines an outward extension direction away from the boundary of the target area, and wherein the extension node is generated by the forward calculation based on the positive value of the extension distance.

9. The autonomous traveling robot according to claim 8, wherein the processor further executes:

extending the extension distance from the target node along the second side for a second node being generated;

defining a parallelogram by a first extension segment from the target node to the first node, a second extension segment from the target node to the second node, and a first included angle between the first extension segment and the second extension segment; and defining a second path node in the traveling path by a plurality of vertices of the parallelogram, wherein the first node, the second node, the target node, and the second path node are the plurality of vertices of the parallelogram.

10. The autonomous traveling robot according to claim 9, wherein the processor further executes: defining the second path node by a sum of a first vector from the target node to the first node and a second vector from the target node to the second node respectively added to coordinates of the target node.

11. The autonomous traveling robot according to claim 8 further comprising:

a sterilizer, coupled to the processor, wherein there are a plurality of path nodes on the traveling path, and the processor further executes:

defining a sequence of the path nodes by an application orientation of the sterilizer.

12. The autonomous traveling robot according to claim 8, further comprising:

a sterilizer, coupled to the processor, wherein the processor executes:

defining the safety distance by an application range of the sterilizer.

13. The autonomous traveling robot according to claim 8, wherein the processor further executes:

receiving a selecting operation of a target object; and defining the edge of the target area by an outline of the target object.

14. The autonomous traveling robot according to claim 8, wherein the processor further executes:

receiving an editing operation on a two-dimensional map, wherein the two-dimensional map is presented on a user interface, and the editing operation comprises adding the target node of the target area; and defining the edge of the target area by the editing operation, wherein the target node is located at the edge of the target area.

* * * * *